(12) United States Patent
Kim et al.

(10) Patent No.: US 7,263,263 B2
(45) Date of Patent: Aug. 28, 2007

(54) METHOD FOR MONITORING SPIN IMPARTED ON OPTICAL FIBER AND METHOD FOR MAKING OPTICAL FIBER BY USING THE SAME

(75) Inventors: Chul-Min Kim, Gyeonggi-do (KR); Myung-Ho Jang, Gyeongsangbuk-do (KR); Sang-Joon Bae, Seoul (KR); Young-Il Kwon, Seoul (KR); Won-Sang Yoo, Gyeonggi-do (KR); Joon-Keun Lee, Seoul (KR)

(73) Assignee: LG Cable, Ltd., Seoul (KR)

( * ) Notice: Subject to any disclaimer, the term of this patent is extended or adjusted under 35 U.S.C. 154(b) by 306 days.

(21) Appl. No.: 10/629,893

(22) Filed: Jul. 29, 2003

(65) Prior Publication Data
US 2004/0042747 A1    Mar. 4, 2004

(30) Foreign Application Priority Data
Aug. 31, 2002    (KR) ............... 2002-52301

(51) Int. Cl.
G02B 6/02    (2006.01)
(52) U.S. Cl. .................................... 385/123
(58) Field of Classification Search ............... 385/123; 65/376–435; 356/73.1
See application file for complete search history.

(56) References Cited

U.S. PATENT DOCUMENTS

| | | | |
|---|---|---|---|
| 5,298,047 A | 3/1994 | Hart et al. ............... 65/3.11 |
| 5,418,881 A | 5/1995 | Hart et al. ............... 385/123 |
| 5,897,680 A | 4/1999 | Geertman ............... 65/402 |
| 5,943,466 A | 8/1999 | Hederson et al. ........... 385/123 |
| 6,148,131 A | 11/2000 | Geertman ............... 385/123 |
| 6,240,748 B1 | 6/2001 | Henderson et al. ........... 65/402 |
| 6,550,281 B1 * | 4/2003 | Hawk ............... 65/402 |
| 6,876,804 B2 * | 4/2005 | Chen et al. ............... 385/123 |

FOREIGN PATENT DOCUMENTS

| | | | |
|---|---|---|---|
| JP | 05024878 A | * | 2/1993 |
| JP | 06227838 A | * | 8/1994 |

* cited by examiner

*Primary Examiner*—Jennifer Doan
(74) *Attorney, Agent, or Firm*—Jones Day

(57) ABSTRACT

A method for monitoring a spin imparted on an optical fiber in order to reduce Polarization Mode Dispersion (PMD) includes the steps of imparting a spin on a high-temperature optical fiber which is drawn from a preform, photographing a dispersion pattern peculiar to the spun optical fiber with a camera from scattered light naturally generated by the spin imparted on the optical fiber, and displaying the photographed dispersion pattern. The method enables monitoring of rate and period of the spin imparted on the optical fiber on the basis of the displayed dispersion pattern.

18 Claims, 9 Drawing Sheets

METHOD FOR MONITORING SPIN IMPARTED ON OPTICAL FIBER AND METHOD FOR MAKING OPTICAL FIBER BY USING THE SAME

BACKGROUND OF THE INVENTION

1. Field of the Invention

The present invention relates to a method for making an optical fiber, and more particularly to a method for monitoring a spin imparted on an optical fiber to reduce Polarization Mode Dispersion(PMD) and ensuring bidirectional symmetry of the spin.

2. Description of the Related Art

A single mode optical fiber with a circular symmetric structure theoretically has two orthogonal polarization modes which are compensated each other. Generally, an electric field of the light propagating through an optical fiber can be considered as linear overlap of such two peculiar polarization modes. In the single mode optical fiber in fact, compensation of the two polarization modes is generated due to defective factors such as symmetric lateral stress or eccentricity of a circular core.

These two modes are propagated at different phase rates, hence two modes have different propagation constants ($\beta_1$ and $\beta_2$). This difference of propagation constants is called double refraction ($\Delta\beta$), and the increase of double refraction means the increase of rate difference between two polarization modes.

Differential time delay between two polarization modes is called Polarization Mode Dispersion (hereinafter, referred to as "PMD"). The presence of PMD is one of factors causing difficulty in high-speed transmission or analog data transmission.

To improve PMD characteristics of the optical fiber, there are significantly handled an optical fiber preform making technique and an optical fiber drawing technique.

The optical fiber preform making technique is directed to lowering PMD of the optical fiber drawn from the preform by increasing the non-circularity of preform.

In addition, the optical fiber drawing technique is directed to lowering PMD by making the optical fiber be twisted with a pitch far less than its beat length so that the polarization modes can be gradually compensated due to relative delay between the modes.

U.S. Pat. Nos. 5,298,047 and 5,418,881 by Hart et al. disclose a method for applying a torque to an optical fiber so that a spin imparted on the optical fiber has non-constant spatial frequency (spins/m) by oscillating a guide roller contacted with the coated optical fiber at a certain angle with respective to a drawing axis or linearly reciprocating the guide roller to a direction perpendicular to the drawing axis. Particularly, Hart el al. report that a spin function applying a torque to the optical fiber is desirably a sine function which imparts alternating spins clockwise and counterclockwise to the optical fiber.

At this point, U.S. Pat. Nos. 5,943,466 and 6,240,748 by Henderson et al. report that the spin function generating a torque to an optical fiber strand is substantially not a sine function, and a time-varying complex function having at least two peak values such as frequency-modulated sine function or amplitude-modulated sine function is more effective to achieve reduction of PMD.

In addition, U.S. Pat. Nos. 5,897,680 and 6,148,131 by Geertman disclose a method for arranging a pair of rotating rollers to be faced each other on the basis of a drawing axis, contacting an optical fiber to the rollers respectively so that the rollers press optical fiber strands, and then rotating the rotating rollers on the center of the optical fiber in order to apply alternating torques clockwise and counterclockwise to the optical fiber.

The conventional spin imparting methods described above are reported to be effective for reduction of PMD in an optical fiber drawing process.

However, even in the above conventional techniques, it is also impossible to measure whether the spin imparted on the optical fiber in the actual process satisfies predetermined spin rates (spins/m) and spin period or not.

But, reliability of the spin imparting function is indirectly determined by measuring PMD of the optical fiber wound around a spool after the drawing process.

The reason that determining whether the spin is reliably imparted during an actual process in the conventional art is impossible is closely related to a spin generating principle of a spin imparting device. In other words, the conventional spin imparting device installs rollers on a path of the optical fiber drawn at a high speed, and then moves the rollers independently of the movement of optical fiber to generate a spin. Thus, the factors affecting on spin generation tend to be easily varied according to process conditions. Therefore, in the conventional art, it is substantially impossible to monitor and measure whether the spin function set at an initial stage of the process is properly operated through an actual process.

Thus, there is still required a method for monitoring a pattern of a spin imparted on the optical fiber during the process execution, determining whether spin period and spin rate based on the spin function are suitably practiced, and controlling the spin period and the spin rate.

SUMMARY OF THE INVENTION

The present invention is designed to overcome drawbacks of the prior art, and an object of the invention is to provide a method for monitoring a spin of an optical fiber in real time.

Another object of the present invention is to provide a method for determining bi-directional symmetry of alternating symmetrical spins imparted on an optical fiber in real time.

In addition, there is also provided a method for reliably realizing a desired spin function in an actual process by controlling a motion of a spin imparting device on the basis of spin patterns monitored during the drawing process.

Other objects and advantages of the present invention are described below, which would be understood with embodiments. In addition, objects and advantages of the present invention can be realized by means mentioned in appended claims and their combinations.

The inventors have found that an optical fiber existing between a heating step and a cooling step during the drawing process contains high thermal energy at least 2,000° C., and this thermal energy can be easily converted into light energy. In addition, when stress is exerted to the optical fiber, this light energy is dispersed outside.

If a spin is imparted on a coated optical fiber during the drawing process, a bare optical fiber before coating is also applied with a spin. Thus, a spin is also imparted on the optical fiber existing between the heating step and the cooling step, and the light energy is dispersed by the spin and then emitted outside. This dispersed light is observed to have a pattern in which bright and dark patterns are crossed, and this pattern has same feature as the spin period.

Thus, the inventors have found that period and rate of the spin imparted on the optical fiber can be monitored by photographing a dispersion pattern of the light dispersed and emitted by the spin.

In order to realize this conception of the inventors, the present invention provides a method for monitoring a spin imparted on an optical fiber which includes the steps of imparting a spin on a high-temperature optical fiber which is drawn from a preform; photographing a dispersion pattern peculiar to the spun optical fiber with a camera from scattered light naturally generated by the spin imparted on the optical fiber; and displaying the photographed dispersion pattern. Thus, rate and period of the spin imparted on the optical fiber can be monitored based on the displayed dispersion pattern.

In addition, the inventors have fount that, in an optical fiber to which alternating symmetrical spins (symmetrical to clockwise and counterclockwise directions) are imparted, bi-directional symmetry of the spins can be determined by obtaining first and second dispersion patterns from clockwise/counterclockwise symmetrical points and then comparing whether the numbers of these dispersion patterns are coincident. The bi-directional symmetry of the spins becomes a standard for determining accuracy of the spin period. In other words, by observing the bi-directional symmetry of the spins, it can be determined whether the actual device is operated to satisfy a predetermined spin function.

In order to realize this conception of the inventors, the present invention provides a method for making an optical fiber which includes the steps of heating an optical fiber preform to a predetermined softening temperature; drawing an optical fiber from the preform; cooling the drawn optical fiber to a temperature suitable for coating; coating at least one polymer layer on the cooled optical fiber; imparting bi-directional symmetric alternating spins on the optical fiber by supplying clockwise/counterclockwise alternating torques to the optical fiber; photographing dispersion patterns peculiar to the spun optical fiber from scattered light naturally generated by the spin imparted on the optical fiber, wherein first and second dispersion patterns are photographed respectively at a first torque point in a clockwise direction and a second torque point in a counterclockwise direction which is symmetric to the first torque point, and determining bi-directional symmetry of the imparted spin by comparing the photographed first and second dispersion patterns.

In addition, the inventors have found that the rate and the period of the spins imparted on the optical fiber can be observed from the dispersion patterns obtained from the optical fiber, and it is also possible to control the spin rate and the spin period of the optical fiber on the basis of the observed results.

In order to realize this conception of the inventors, the present invention provides a method for controlling a spin imparted on an optical fiber which includes the steps of imparting circumferential spin on a high-temperature optical fiber drawn from a preform; obtaining dispersion pattern data peculiar to the spun optical fiber from scattered light naturally generated from the spin imparted on the optical fiber; and controlling rate and period of the spin imparted on the optical fiber on the basis of the obtained dispersion pattern data.

BRIEF DESCRIPTION OF THE DRAWINGS

These and other features, aspects, and advantages of the present invention will become better understood with regard to the following description, appended claims, and accompanying drawings, in which like components are referred to by like reference numerals. In the drawings:

DETAILED DESCRIPTION OF THE PREFERRED EMBODIMENT

Figure 1:
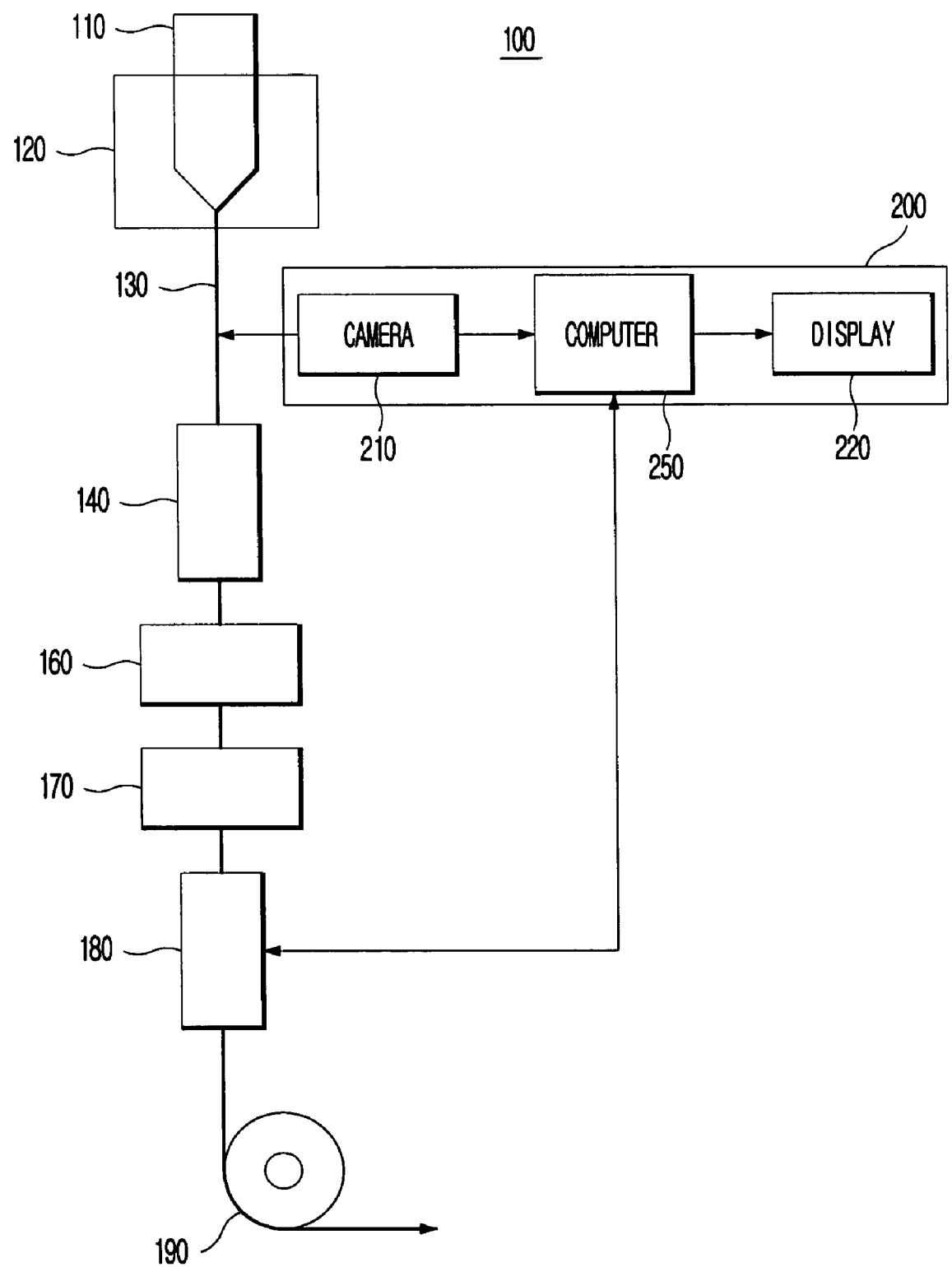
FIG. 1 is a schematic view showing an optical fiber making apparatus according to the present invention.

Hereinafter, preferred embodiments of the present invention will be described in detail with reference to the accompanying drawings. FIG. 1 shows schematic configuration of an optical fiber making apparatus 100 according to the present invention.

An optical fiber preform 110 is slowly supplied to a melting furnace 120, and an optical fiber 130 is drawn from a neck-down portion of the preform. A bare optical fiber (or, an uncoated optical fiber) drawn as above is supplied to a coating device 160 through a cooling device 140 where a coating polymer is coated on the comparatively cooled bare optical fiber, and the optical fiber then passes through a hardening device 170. Typically, the hardening device 170 has a UV lamp. A spin imparting device 180 and a driving unit 190 such as a capstan are provided downstream of the hardening device 170. A draw force for the optical fiber is provided from the capstan 190, from which the optical fiber is typically advanced to a winding unit such as a take-up spool.

Figure 2A:
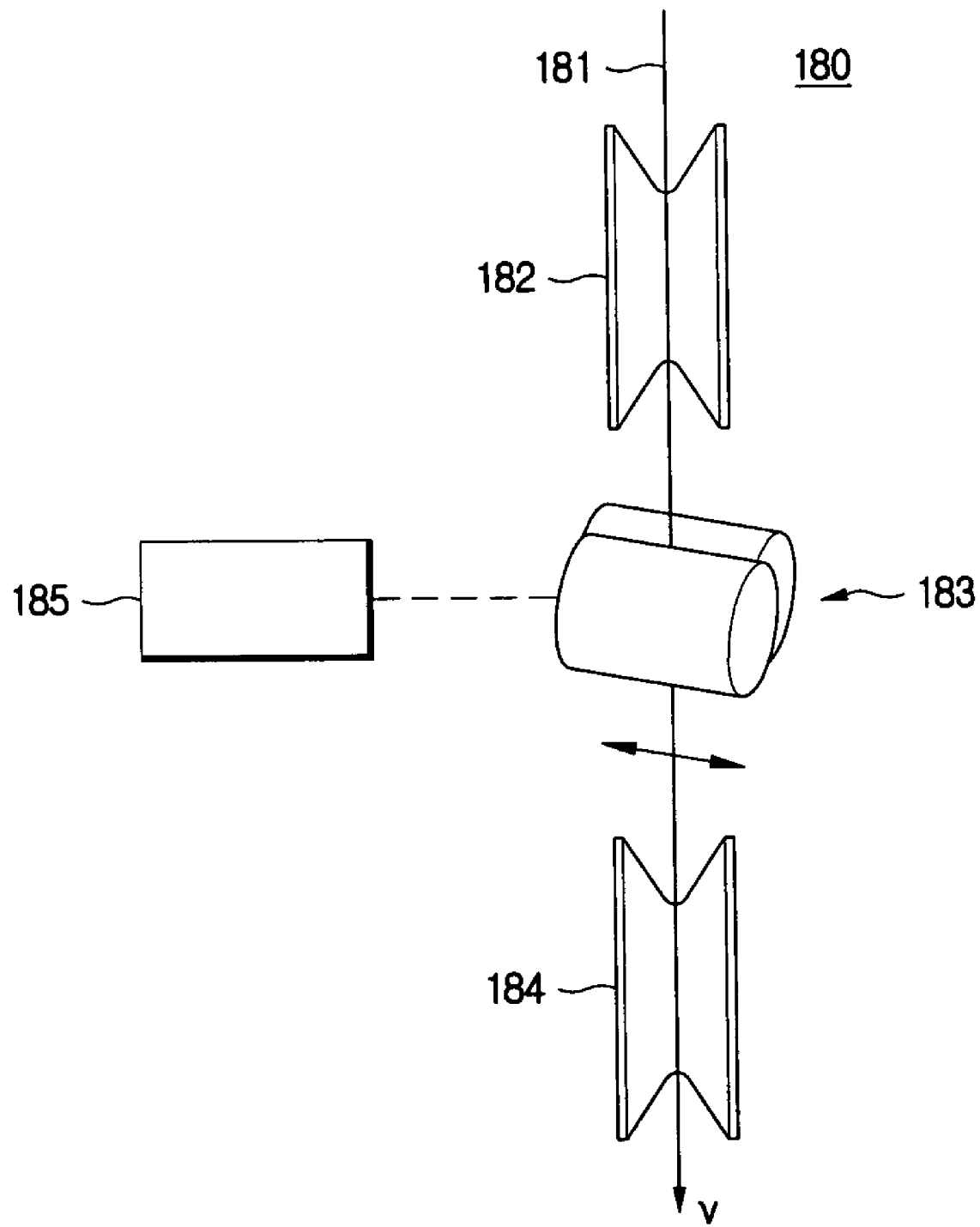
FIGS. 2a to 2c are schematic views showing a spin imparting device used in the apparatus of FIG. 1.
Figure 2B:
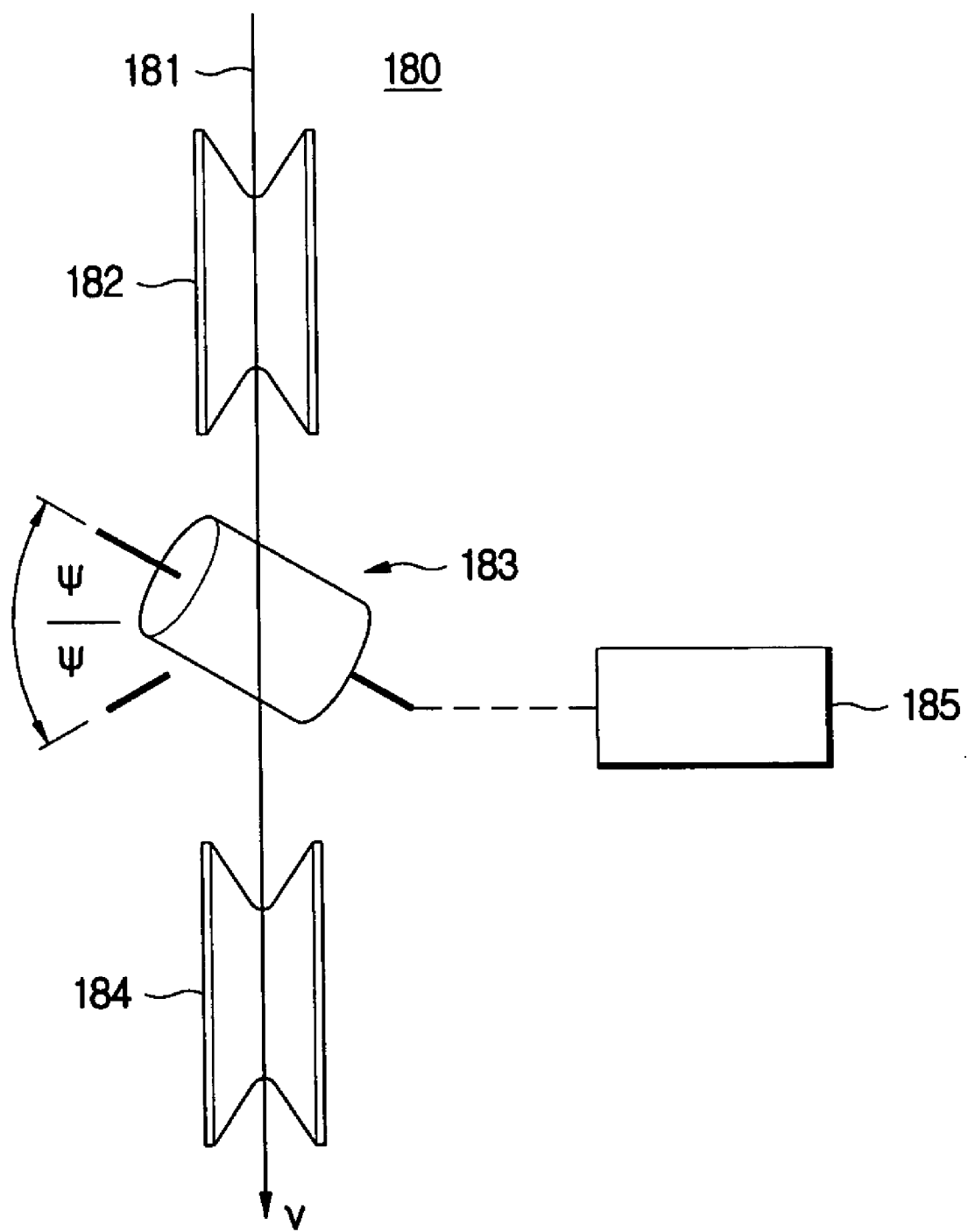
Figure 2C:
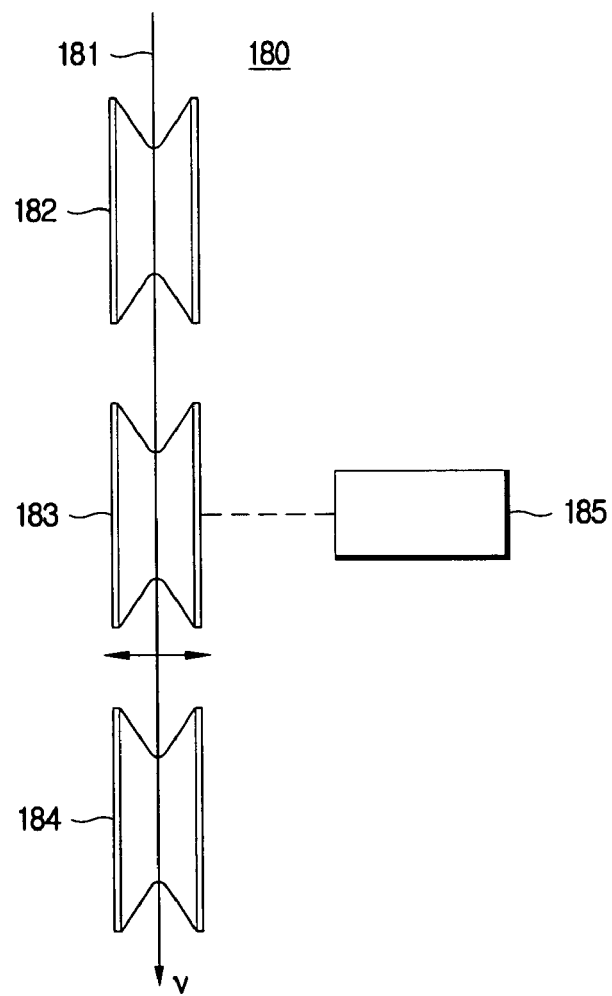

The spin imparting device 180 provides a rotating torque to the coated optical fiber in order to impart a spin on the optical fiber drawn from the preform. This spin imparting device is shown in FIGS. 2a to 2c in detail.

The optical fiber making apparatus 100 of the present invention also includes a spin monitoring and controlling system denoted with reference numeral 200.

The spin monitoring and controlling system 200 basically includes a camera 210, a computer 250 and a display 220. The camera 210 is typically an analog camera. At least one camera is installed between the melting furnace 120 and the coating device 160, more preferably between the melting furnace 120 and the cooling device 140, and photographs 1~10 m range of the optical fiber.

At this time, the optical fiber 130 is a bare optical fiber, before coated, after heated over 2,000° C. in the melting furnace 120, and a predetermined spin is imparted on the optical fiber 130 from the spin imparting device 180 disposed downstream. In addition, at this time, the thermal energy inherent in the optical fiber 130 is converted into light energy, and the optical fiber 130 emits scattered light due to the spin imparted on the optical fiber. Thus, the camera 210 may photograph a dispersion pattern image of the optical fiber within a range of 1~10 m, preferably 5 m. The dispersion pattern image photographed at this time has a shape in which bright and dark patterns are crossed as shown in FIG. 5.

The dispersion pattern image photographed by the camera 120 is input to the computer 250, which processes the dispersion pattern image into a displayable formation and then outputs through the display 220 such as a monitor.

Therefore, a worker may observe a pattern of the spin (or, spin rate, spin period, or the like) imparted on the optical fiber just by checking the dispersion pattern image displayed through the display 220. If the dispersion pattern image displayed on the display 220 is not matched with a desired spin pattern, the worker may achieve a desired spin function by controlling a motion of the spin imparting device 180.

Now, a specified embodiment of the spin imparting device 180 used in the apparatus 100 of the present invention is described with reference to FIGS. 2a to 2c.

Figure 3:
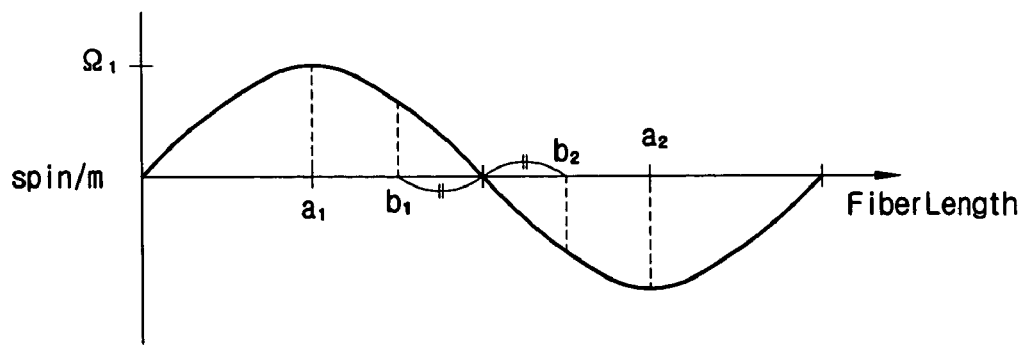
FIG. 3 is a graph illustrating a spin function of alternating spins imparted by the spin imparting device of FIGS. 2a to 2c.

A spin imparting device 180 shown in FIG. 2a imparts a spin on the optical fiber by making a pair of rollers 183, of which a rotating axis is perpendicular to a drawing direction (v) of the optical fiber, be contacted with a coated optical fiber 181 and then translating the rollers 183 each other. At this time, the rollers should be rotated to opposite directions each other. This device may impart alternating symmetric spins clockwise and counterclockwise on the optical fiber as shown in FIG. 3. Of course, it is also possible to generate a spin to only one direction by restricting movement of the rollers to any side on the basis of the drawing axis. In addition, it is also possible to set the spin function not in a sine function as shown in FIG. 3 but in an amplitude-modulated sine function or a frequency-modulated sine function by controlling a driving unit 185 which controls drive of the rollers.

In addition, a spin imparting device 180 shown in FIG. 2b imparts alternating symmetric spins having a shape of FIG. 3 by oscillating the rollers 183, contacting with the optical fiber 181, at a predetermined angle ($\Psi$) on the center of its rotating axis, similar to the case of FIG. 2a. Of course, this device can also impart a spin to one direction, and its spin function can be set as an amplitude-modulated sine function or a frequency-modulated sine function by controlling the driving unit 185.

Finally, a spin imparting device 180 shown in FIG. 2c imparts alternating symmetric spins having a shape of FIG. 3 by vertically reciprocating the rollers 183, contacting with the optical fiber 181, at constant amplitude and frequency on the center of the drawing direction (v). This device can also impart a spin to one direction, and its spin function can be set as an amplitude-modulated sine function or a frequency-modulated sine function by controlling the driving unit 185, as in the case of FIG. 2b.

In FIGS. 2a to 2c, reference numerals 182 and 184 denote guide rollers for guiding the optical fiber not to be departed beyond a predetermined deviation from the drawing axis.

Now, detailed configuration of the spin monitoring and controlling system used in the apparatus of the present invention is described with reference to FIG. 4.

Figure 4:
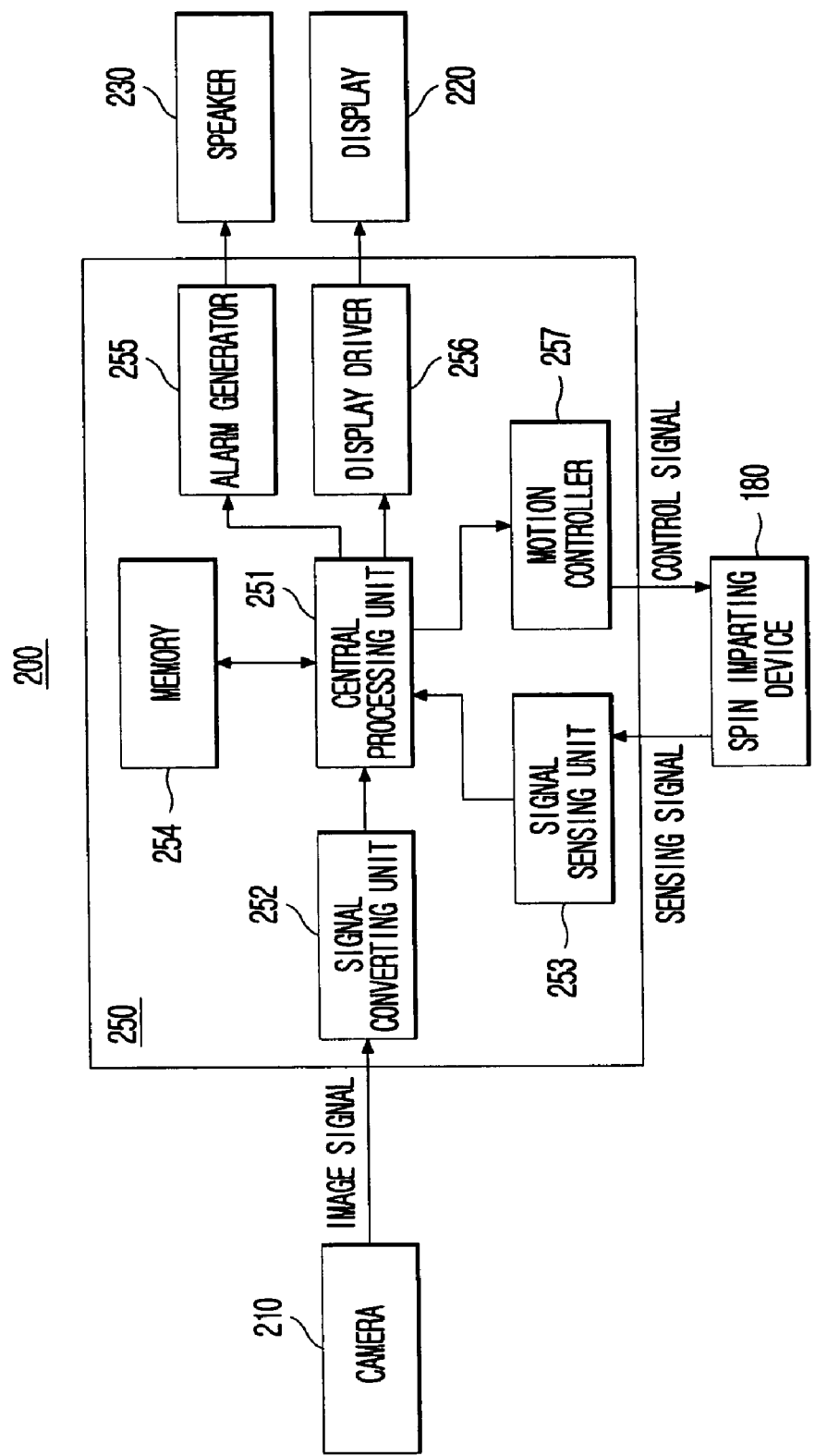
FIG. 4 is a block diagram showing a spin monitoring and controlling system according to the present invention.

As shown in FIG. 4, the spin monitoring and controlling system 200 according to the present invention includes a camera 210, a computer 250, a speaker 230 and a display 220.

The computer 250 also includes a central processing unit 251, a signal converting unit 252, a display driver 256, an alarm generator 255, a memory 254, a signal sensing unit 253 and a motion controller 257.

The signal converting unit 252 converts a dispersion pattern image, input from the camera 210, into a digital signal which the central processing unit 251 is able to recognize.

The memory 254 has RAM for storing input data such as the dispersion pattern image input from the camera 210 or other various output data and ROM for storing program to be loaded on the central processing unit 251.

The program stored in the memory 254 processes the dispersion pattern image from the camera 210 into a formation which can be output from the display 220, extracts first and second dispersion patterns on the basis of signals sensed at symmetric torque points $a_1$, and $a_2$ or $b_1$, and $b_2$ of FIG. 3 input from the signal sensing unit 253, and then compares the first and second dispersion patterns to determine bi-directional symmetry of the spin imparted on the optical fiber.

This program calculates motion control signals such as X-axis or Y-axis travels of the roller and a gyratory center point of the roller on the ground of a spin rate or the bi-directional symmetry of the spin based on the dispersion patterns. In addition, this program may calculate spin control signals such as amplitude or vibrating rate of the roller on the basis of the dispersion pattern data.

The central processing unit 251 loads and executes the program stored in the memory 254.

The signal sensing unit 253 is an input interface which receives a sensing signal from a sensor (not shown) installed to the spin imparting device 180 and then transmits the signal to the central processing unit 251. This sensing signal can be a sensing data related to a moving position or a moving speed of the roller. In this case, the sensor is a position sensor or a velocity sensor.

Particularly, in case the system of the present invention determines bi-directional symmetry of the spin, torque points can be respectively set clockwise and counterclockwise arbitrarily, as shown in FIG. 3. For example, this torque points can be set to peak torque points such as $a_1$, and $a_2$ points of FIG. 3 or other symmetric point such as $b_1$ and $b_2$. However, at least one torque point should be selected in both clockwise and counterclockwise directions, and a pair of the selected torque points should be symmetric each other. Thus, the numbers of the photographed dispersion patterns at the symmetric torque points should be coincident. If the numbers of dispersion patterns are not coincident, it means that the spin imparted on the optical fiber is not symmetric clockwise and counterclockwise, and this indicates that a center of the roller applying a torque to the optical fiber is tilted to the drawing axis or deviated in X-axis.

Sensing the torque points can be achieved by installing a sensor (not shown) such as a photo sensor at a predetermined position. For example, if the spin imparting device has a shape shown in FIG. 2c, the sensor would be installed on a vibrating path of the roller 183, which is laterally symmetrical to the drawing axis. In particular, if the torque points were peak torque points such as $a_1$, and $a_2$ points of FIG. 3, the sensor would be installed to a maximum amplitude point of the roller 183.

If the roller 183 moves to apply a torque to the optical fiber as shown in FIGS. 2a to 2c while the sensor is installed on a moving path of the roller 183, the sensor generates a sensing signal as soon as the roller reaches the predetermined torque point, and then transmits the signal to the signal sensing unit 253.

At the instant that the sensing signal is input to the signal sensing unit 253, the central processing unit 251 addresses dispersion pattern images from the camera 210 into first and second dispersion pattern images, and then stores them in the memory 254.

The first and second dispersion pattern images stored as above are used later to determine bi-directional symmetry of the spin.

The display driver 256 is used to control the display 220.

The alarm generator 255 generates an alarm according to a command of the central processing unit 251 and transmits the alarm to the speaker 230.

The motion controller 257 controls various objects existing in the spin imparting device such as a rotary motor or a servo motor on the basis of compensation signals calculated in the central processing unit. For example, in case of controlling bi-directional symmetry of the spin, particularly as shown in FIG. 2c, the motion controller 257 controls the roller 183 to be always positioned at the center by adjusting a motor (not shown) for moving the roller 183 to an X-axis direction perpendicular to the drawing axis or a motor (not shown) for tilting the roller 183 on the center of the rotating axis.

Hereinafter, a method for making an optical fiber according to the present invention is described based on the above-mentioned configuration of the apparatus.

Figure 6:
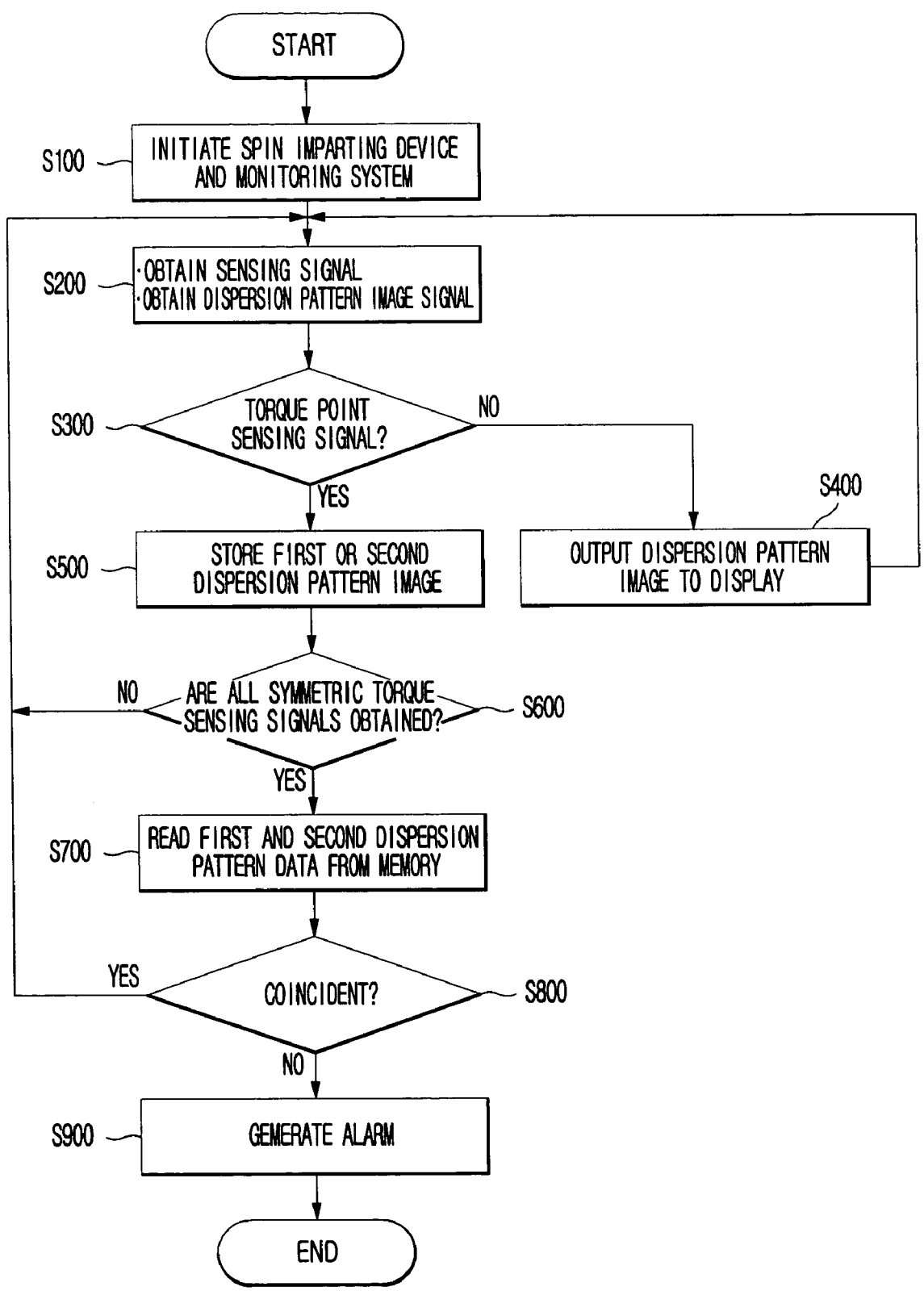
FIG. 6 is a flow chart for illustrating a method for monitoring and controlling a spin according to the present invention.

FIG. 6 is a flow chart for illustrating a method for monitoring and controlling a spin according to the present invention.

Ahead of executing the optical fiber drawing process, the spin imparting device 180 of FIGS. 2a to 2c and the spin monitoring and controlling system 200 of FIG. 4 installed to the optical fiber making apparatus are initialized in advance. (step S100)

Then, with a bare optical fiber drawn from an optical fiber preform and coated with polymer, alternating symmetric spins in clockwise and counterclockwise directions are imparted on the coated optical fiber by using the device shown in FIGS. 2a to 2c. Hence, the camera 210 installed between the melting furnace 120 and the coating device 160, or more preferably between the melting furnace 120 and the cooling device 140, photographs the optical fiber 130 passing through a predetermined area to obtain a dispersion pattern image and then inputs this image to the computer 250. In addition, the signal sensing unit 253 acquires a torque point sensing signal from the sensor of the spin imparting device 180. (step S200)

The central processing unit 251 receiving the dispersion pattern image from the camera 210 determines whether there is input a sensing signal from the signal sensing unit 253 at the instant that the dispersion pattern is input. (step S300) Then, the central processing unit 251 outputs the input dispersion pattern image as it is to the display 220 if there exists no sensing signal. (step S400)

On the other hand, if there exists an input of a torque point sensing signal at the signal sensing unit in the step S300, the input dispersion pattern image is addressed into first and second dispersion patterns and then stored in the memory 254. (step S500)

After that, the central processing unit 251 determines whether all symmetric torque point sensing signals are obtained for one cycle. (step S600) If signals are not all obtained, the process is returned to the step S200 and the above routine is repeated. Contrarily, if all symmetric torque point sensing signals are obtained for one cycle, the central processing unit 251 reads image data of the first and second dispersion patterns from the memory 254. (step S700)

Figure 5A:
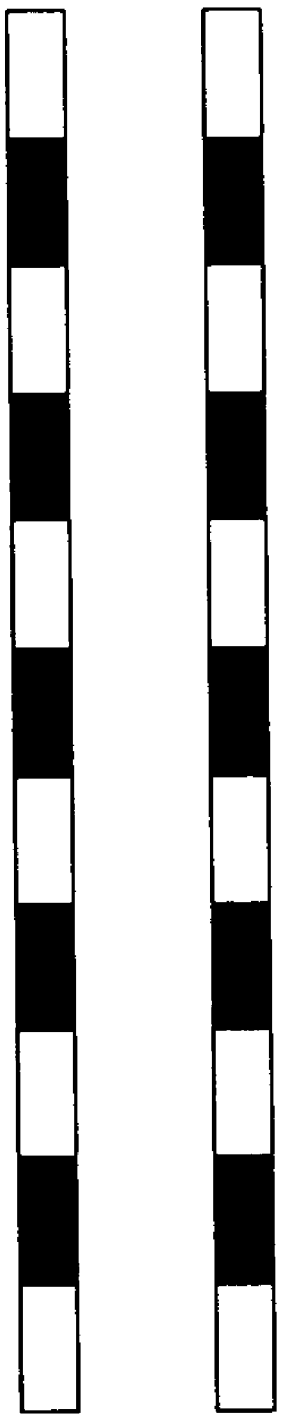
FIGS. 5A, 5B and 5C dispersion pattern images photographed by a camera.
Figure 5B:
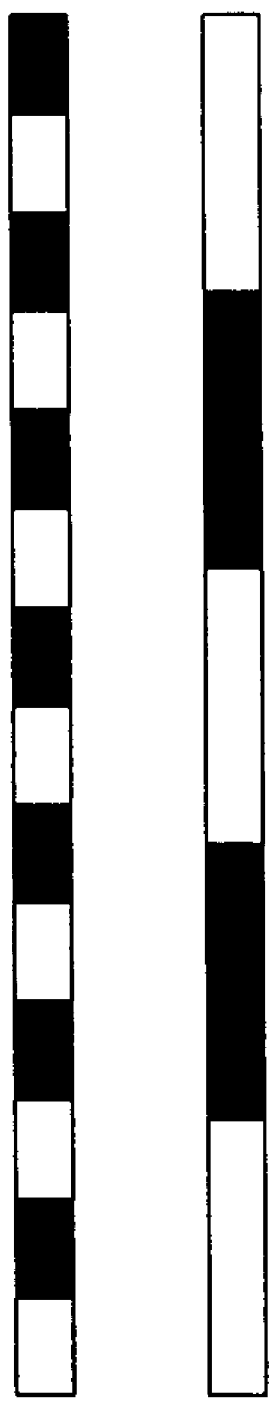
Figure 5C:
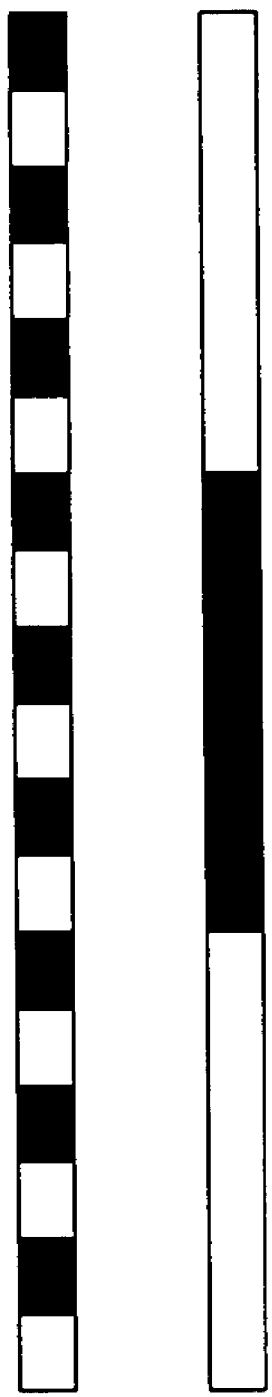

After reading the first and second dispersion patterns from the memory 254, the central processing unit 251 determines whether the numbers of these dispersion patterns are coincident. For example, the central processing unit 251 determines that the numbers are coincident if the first and second dispersion patterns are as shown in FIG. 5a, in which the first dispersion patterns are five and the second dispersion patterns are five. However, the central processing unit 251 determines that the numbers are not coincident if the first and second dispersion patterns are as shown in FIG. 5b, in which the first dispersion patterns are seven and the second dispersion patterns are two, or as shown in FIG. 5c, in which the first dispersion patterns are nine and the second dispersion pattern is one. (step S800).

FIG. 5a shows a dispersion pattern image photographed at $a_1$ and $a_2$ points, viz. at peak torque points. The first and second dispersion patterns are preferably obtained from the peak torque points since the peak torque points are more advantageous than other symmetric torque points, e.g. $b_1$, and $b_2$ in FIG. 3, in light of setting of torque points, installation of the sensor, photographing of the optical fiber or the like.

If it is determined that the numbers of the first and second dispersion patterns are coincident in the step S800 (FIG. 5a), it is also determined that the bi-directional symmetry of the spin is satisfactory, and then the routine from the step S200 to the step S800 is repeated.

On the other hand, if the step S800 determines that the numbers of the first and second dispersion patterns are not coincident (FIGS. 5b and 5c), it is determined that the bi-directional symmetry of the spin is not satisfactory, and then an alarm is generated through the speaker 230 to inform this fact outside (step S900).

Meanwhile, it is also possible that the step S900 compares the numbers of the first and second dispersion patterns, calculates a compensation control signal required for adjusting a center of the roller 183 applying a torque to the optical fiber 181, and then transmits this signal to the motion controller 257. At this time, the motion controller 257 may adjust a center of the roller by applying a drive control signal to a motor which corrects an X-axis position of the roller 183 and a motor which corrects an inclination of a rotating axis of the roller.

When there is a problem in the spin period, the embodiment of FIG. 6 informs this fact outside through an alarm. However, the present invention is not limited to that case, and can be variously modified within ordinary knowledge of those skilled in the art if it may notice the problem outside.

APPLICABILITY TO THE INDUSTRY

The method of the present invention makes it possible to easily adjust a spin rate and a spin period since a pattern of the spin imparted on the optical fiber can be monitored in real time during the optical fiber drawing process. Thus, it is possible to reduce PMD of an optical fiber to a desired level.

In addition, the present invention enables to monitor bi-directional symmetry of the spin imparted on the optical fiber and give warning. Thus, it becomes possible to set an optimal spin imparting condition depending on new work conditions or preform conditions.

The preferred embodiments of the present invention are described as above with reference to the accompanying drawings. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A method for monitoring a spin imparted on an optical fiber comprising the steps of:
    imparting a spin on a high-temperature optical fiber which is drawn from a preform;
    photographing a dispersion pattern peculiar to the spun optical fiber with a camera from scattered light naturally generated by the spin imparted on the optical fiber; and
    displaying the photographed dispersion pattern, wherein a form of the spin imparted on the optical fiber is monitored based on the displayed dispersion pattern.

2. A method for monitoring a spin imparted on an optical fiber according to claim 1, wherein the monitoring of dispersion pattern is targeted for a bare optical fiber which is not yet coated with polymer.

3. A method for monitoring a spin imparted on an optical fiber according to claim 2, wherein the monitoring of dispersion pattern is targeted for an optical fiber which is in a state between a preform heating process and an optical fiber cooling process.

4. A method for making an optical fiber comprising the steps of:
    (a) heating an optical fiber preform to a predetermined softening temperature;
    (b) drawing an optical fiber from the preform;
    (c) cooling the drawn optical fiber to a temperature suitable for coating;
    (d) coating at least one polymer layer on the cooled optical fiber;
    (e) imparting bi-directional symmetric alternating spins on the optical fiber by supplying clockwise/counterclockwise alternating torques to the optical fiber;
    (f) photographing dispersion patterns peculiar to the spun optical fiber from scattered light naturally generated by the spin imparted on the optical fiber; and
    wherein first and second dispersion patterns are photographed respectively at a first torque point in a clockwise direction and a second torque point in a counterclockwise direction which is symmetric to the first torque point,
    (g) determining bi-directional symmetry of the imparted spin by comparing the photographed first and second dispersion patterns.

5. A method for making an optical fiber according to claim 4, wherein the first torque point is a peak clockwise torque point, and the second torque point is a peak counterclockwise torque point.

6. A method for making an optical fiber according to claim 4, further comprising the step of: (h) generating an alarm outside when the first and second dispersion patterns are not coincident in the step (g).

7. A method for making an optical fiber according to claim 6, wherein the photographing of dispersion patterns is conducted using a camera, and wherein at least one camera is installed between a preform heating device and an optical fiber coating device.

8. A method for making an optical fiber according to claim 7, wherein at least one camera is installed between the preform heating device and an optical fiber cooling device.

9. A method for making an optical fiber according to claim 8, wherein the determination of bi-directional symmetry of the spin is conducted using a computer connected to the camera, and wherein the computer compares the pattern number of the first dispersion pattern image obtained from the camera with the pattern number of the second dispersion pattern image obtained from the camera, and determines the bi-directional symmetry of the spin on the basis of the coincidence of the numbers.

10. A method for making an optical fiber according to claim 6, wherein the alternating torques is provided by vibrating a driving roller, contacting with the optical fiber, on the center of an axis substantially parallel to a drawing direction of the optical fiber.

11. A method for making an optical fiber according to claim 6, wherein the alternating torques is provided by vibrating a driving roller, contacting with the optical fiber, with being tilted from an axis substantially parallel to a drawing direction of the optical fiber.

12. A method for controlling bi-directional symmetry of alternating symmetrical spins imparted on an optical fiber in an optical fiber making process including the steps of:
    (a) heating an optical fiber preform to a predetermined softening temperature;
    (b) drawing an optical fiber from the preform;
    (c) cooling the drawn optical fiber to a temperature suitable for coating;
    (d) coating at least one polymer layer on the cooled optical fiber; and
    (e) imparting clockwise/counterclockwise alternating spins on the optical fiber by contacting the coated optical fiber to a guide roller and then vibrating the guide roller on the center of an axis substantially parallel to a drawing axis, wherein the method comprises the steps of:
    photographing dispersion patterns peculiar to the spun optical fiber from scattered light naturally generated by the spin imparted on the optical fiber; and
    wherein first and second dispersion patterns are photographed respectively at a first torque point in a clockwise direction of the optical fiber and a second torque point in a counterclockwise direction which is symmetric to the first torque point, rearranging a center of the guide roller relative to the drawing axis and the rotating axis so that the number of the photographed first dispersion patterns is coincident with the number of the photographed second dispersion patterns.

13. A method for controlling bi-directional symmetry of alternating symmetrical spins imparted on an optical fiber according to claim 12, wherein the rearrangement of the center of the guide roller is performed by minutely moving the guide roller to a direction perpendicular to the drawing axis or tilting the guide roller minutely on the center of the rotating axis.

14. A method for controlling bi-directional symmetry of alternating symmetrical spins imparted on an optical fiber according to claim 13, wherein the first and second torque points are respectively peak torque points in clockwise/counterclockwise directions.

15. A method for controlling bi-directional symmetry of alternating symmetrical spins imparted on an optical fiber according to claim 14, wherein the rearrangement of the center of the guide roller is performed by driving and controlling a motor for moving the guide roller to a direction perpendicular to the drawing axis and a motor for tilting the guide roller a predetermined angle on the center of the rotating axis;
    wherein the control of the motors is conducted using a computer connected to the camera; and wherein the computer compares the pattern numbers of the first and second dispersion pattern images obtained from the camera, calculates a required travel of the guide roller center when the numbers are not coincided, and drives and controls the motors on the basis of the calculation.

16. A method for controlling bi-directional symmetry of alternating symmetrical spins imparted on an optical fiber according to claim 15, wherein the alternating spins are provided by vibrating a driving roller, contacted with the optical fiber, on the center of an axis substantially parallel to the drawing direction of the optical fiber.

17. A method for controlling bi-directional symmetry of alternating symmetrical spins imparted on an optical fiber according to claim 13, wherein the photographing of dispersion patterns is conducted using a camera, and wherein at least one camera is installed between a preform heating device and an optical fiber coating device.

18. A method for controlling bi-directional symmetry of alternating symmetrical spins imparted on an optical fiber according to claim 17, wherein the alternating spins are provided by vibrating a driving roller, contacted with the optical fiber, with being tilted as much as an angle $\theta$ from an axis substantially parallel to the drawing direction of the optical fiber.

* * * * *